US010102476B2

(12) United States Patent
Caraviello et al.

(10) Patent No.: US 10,102,476 B2
(45) Date of Patent: Oct. 16, 2018

(54) APPLICATION OF MACHINE LEARNING METHODS FOR MINING ASSOCIATION RULES IN PLANT AND ANIMAL DATA SETS CONTAINING MOLECULAR GENETIC MARKERS, FOLLOWED BY CLASSIFICATION OR PREDICTION UTILIZING FEATURES CREATED FROM THESE ASSOCIATION RULES

(75) Inventors: Daniel Z. Caraviello, Indianapolis, IN (US); Rinkal Patel, Indianapolis, IN (US); Reetal Pai, Carmel, IN (US)

(73) Assignee: Agrigenetics, Inc., Indianapolis, IN (US)

( * ) Notice: Subject to any disclaimer, the term of this patent is extended or adjusted under 35 U.S.C. 154(b) by 73 days.

(21) Appl. No.: 12/793,138

(22) Filed: Jun. 3, 2010

(65) Prior Publication Data

US 2010/0332430 A1    Dec. 30, 2010

Related U.S. Application Data

(60) Provisional application No. 61/221,804, filed on Jun. 30, 2009.

(51) Int. Cl.
| G06N 5/00 | (2006.01) |
| G06F 19/18 | (2011.01) |
| A01H 1/04 | (2006.01) |
| G06N 5/02 | (2006.01) |

(52) U.S. Cl.
CPC ............ *G06N 5/025* (2013.01); *A01H 1/04* (2013.01); *G06F 19/18* (2013.01)

(58) Field of Classification Search
CPC ............ C12N 15/8262; C12N 15/8241; C12Q 1/6895; C12Q 1/6869; C12Q 2600/13; G06F 19/18; G06F 19/24; G06F 19/14
See application file for complete search history.

(56) References Cited

U.S. PATENT DOCUMENTS

2005/0144664 A1    6/2005  Smith et al.
2008/0140602 A1    6/2008  Roth et al.

FOREIGN PATENT DOCUMENTS

| CA | 2180386 | 1/1998 |
| CN | 101151615 A | 3/2008 |
| RU | 2215406 | 11/2003 |
| WO | WO02/080079 | 10/2002 |
| WO | 03/040949 A1 | 5/2003 |
| WO | 2008156214 | 9/2007 |

OTHER PUBLICATIONS

Yu et al. Genetic association mapping and genome organization of maize Current Opinion in Biotechnology vol. 17, pp. 155-160 (2006).*
Thabtah et al. MCAR: Multi-class Classification based on Association Rule The 3rd ACSI IEEE International Conference on computer Systems and Applications pp. 1-7 (2005).*
Zheng et al. Real World Performance of Association Rule Algorithms Proceedings of the Seventh ACM SIGKDD International Conference o Knowledge Discovery and Data Mining pp. 401-406 (2001).*
Zhao et al. Comparison of decision tree methods for finding active objects Advances in Space Research vol. 41 pp. 1955-1959 (2008).*
Palaisa et al. Contrasting Effects fo Selection on Sequence Diversity and Linkage Disequilibrium at Two Phytoene Synthase Loci The Plant Cell vol. 15, pp. 1795-1806 (2003).*
Nelson et al. Plant nuclear factor Y (NF-Y) B subunits confer drought tolerance and lead to improved corn yields on water-limited acres Proceedings of the National Academy of Sciences USA vol. 104 pp. 16450-16455 (2007).*
Thornsberry et al. Dwarf8 polymorphisms associate with variation in flowering time Nature Genetics vol. 28 pp. 286-289 (2001).*
Bewick et al. statistics review 13: Receiver operating characteristic curves Critical Care vol. 8, pp. 508-512 (2004).*
Stuber et al. Identification of Genetic Factors Contributing to Heterosis in a Hybrid From Two Elite Maize Inbred Lines Using Molecular Markers Genetics vol. 132 pp. 823-839 (1992).*
Bouchez et al. Marker-Assisted Introgression of Favorable Alleles at Quantitative Trait Loci Between Maize Elite Lines Genetics vol. 162, pp. 1945-1959 (2002).*
PCT International Search Report and Written Opinion for International Application No. PCT/US2010/037211, dated Oct. 19, 2010.
Malovini33 Alberto et al., "Phenotype forecasting with SNPs data through gene-based Bayesian networks" BMC Bioinformatics, Feb. 5, 2009, 9 pages, vol. 10, No. Suppl 2.
Long A D et al., "The power of association studies to detect the contribution of candidate genetic loci to variation in complex traits" Genome Research, Aug. 1, 1999, pp. 720-731, vol. 9.
Agrawal R et al., "Mining association rules between sets of items in large databases" Sigmod Record, Jun. 1, 1993, pp. 207-216, vol. 22, No. 2.
Finding frequent sets and association rules,13.3.2 In: Hand, Mannila, Smyth: "Principles of data Mining" 2006 Cambridge, MIT Press, pp. 433-435.
Xialoi Tang, "Study on Several Mining Methods of Gene Expression Data", Thesis for a Master's Degree of Yangzhou University, Chapter V, Dec. 15, 2007.

* cited by examiner

*Primary Examiner* — John S Brusca
(74) *Attorney, Agent, or Firm* — Magleby Cataxinos & Greenwood

(57) ABSTRACT

The disclosure relates to the use of one or more association rule mining algorithms to mine data sets containing features created from at least one plant or animal-based molecular genetic marker, find association rules and utilize features created from these association rules for classification or prediction.

21 Claims, 1 Drawing Sheet

Area under the ROC curve, before and after adding the new features from step (b).
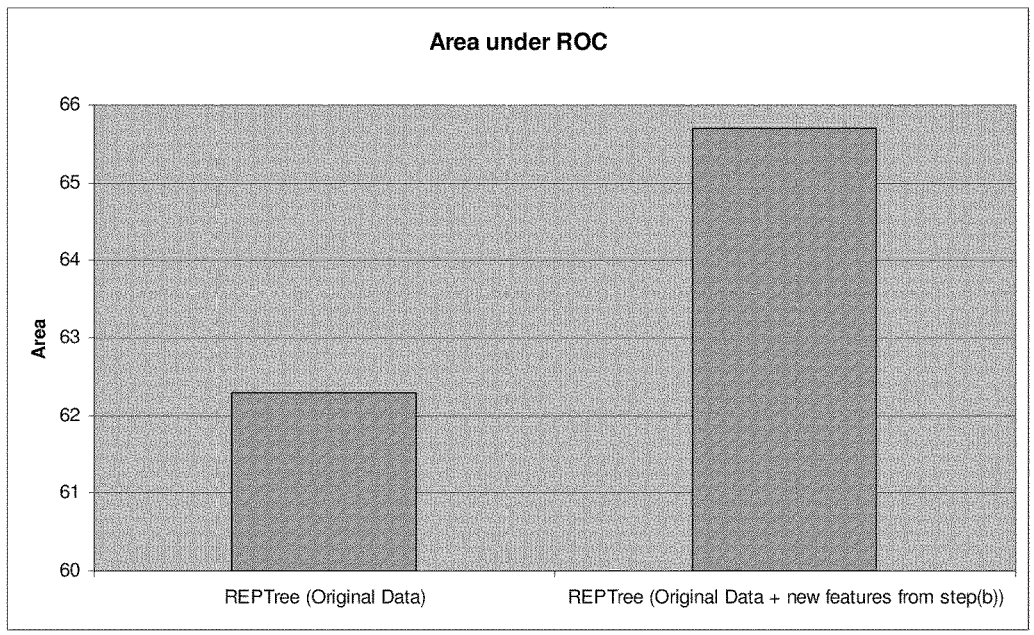

APPLICATION OF MACHINE LEARNING METHODS FOR MINING ASSOCIATION RULES IN PLANT AND ANIMAL DATA SETS CONTAINING MOLECULAR GENETIC MARKERS, FOLLOWED BY CLASSIFICATION OR PREDICTION UTILIZING FEATURES CREATED FROM THESE ASSOCIATION RULES

This application claims a priority based on provisional application 61/221,804 which was filed in the U.S. Patent and Trademark Office on Jun. 30, 2009, the entire disclosure of which is hereby incorporated by reference.

FIELD

The disclosure relates to the use of one or more association rule mining algorithms to mine data sets containing features created from at least one plant or animal-based molecular genetic marker, find association rules and utilize features created from these association rules for classification or prediction.

BACKGROUND

One of the main objectives of plant and animal improvement is to obtain new cultivars that are superior in terms of desirable target features such as yield, grain oil content, disease resistance, and resistance to abiotic stresses.

A traditional approach to plant and animal improvement is to select individual plants or animals on the basis of their phenotypes, or the phenotypes of their offspring. The selected individuals can then, for example, be subjected to further testing or become parents of future generations. It is beneficial for some breeding programs to have predictions of performance before phenotypes are generated for a certain individual or when only a few phenotypic records have been obtained for that individual.

Some key limitations of methods for plant and animal improvement that rely only on phenotypic selection are the cost and speed of generating such data, and that there is a strong impact of the environment (e.g., temperature, management, soil conditions, day light, irrigation conditions) on the expression of the target features.

Recently, the development of molecular genetic markers has opened the possibility of using DNA-based features of plants or animals in addition to their phenotypes, environmental information, and other types of features to accomplish many tasks, including the tasks described above.

Some important considerations for a data analyses method for this type of datasets are the ability to mine historical data, to be robust to multicollinearity, and to account for interactions between the features included in these datasets (e.g. epistatic effects and genotype by environment interactions). The ability to mine historical data avoids the requirement of highly structured data for data analyses. Methods that require highly structured data, from planned experiments, are usually resource intensive in terms of human resources, money, and time. The strong environmental effect on the expression of many of the most important traits in economically important plants and animals requires that such experiments be large, carefully designed, and carefully controlled. The multicollinearity limitation refers to a situation in which two or more features (or feature subsets) are linearly correlated to one another. Multicollinearity may lead to a less precise estimation of the impact of a feature (or feature subset) on a target feature and consequently biased predictions.

A framework based on mining association rules and using features created from these rules to improve prediction or classification, is suitable to address the three considerations mentioned above. Preferred methods for classification or prediction are machine learning methods. Association rules can therefore be used for classification or prediction for one or more target features.

The approach described in the present disclosure relies on implementing one or more machine learning-based association rule mining algorithms to mine datasets containing at least one plant or animal molecular genetic marker, create features based on the association rules found, and use these features for classification or prediction of target features.

SUMMARY

In an embodiment, methods to mine data sets containing features created from at least one plant-based molecular genetic marker to find at least one association rule and to then use features created from these association rules for classification or prediction are disclosed. Some of these methods are suitable for classification or prediction with datasets containing plant and animal features.

In an embodiment, steps to mine a data set with at least one feature created from at least one plant-based molecular genetic marker, to find at least one association rule, and utilizing features created from these association rules for classification or prediction for one or more target features include:

(a) detecting association rules;

(b) creating new features based on the findings of step (a) and adding these features to the data set;

(c) model development for one or more target features with at least one feature created using the features created on step (b);

(d) selecting a subset of features from features in the data set; and (e) detecting association rules from spatial and temporal associations using self-organizing maps (see Teuvo Kohonen (2000), Self-Organizing Map, Springer, 3rd edition.)

In an embodiment, a method of mining a data set with one or more features is disclosed, wherein the method includes using at least one plant-based molecular marker to find at least one association rule and utilizing features created from these association rules for classification or prediction, the method comprising the steps of: (a) detecting association rules, (b) creating new features based on the findings of step (a) and adding these features to the data set; (c) selecting a subset of features from features in the data set.

In an embodiment, association rule mining algorithms are utilized for classification or prediction with one or more machine learning algorithms selected from: feature evaluation algorithms, feature subset selection algorithms, Bayesian networks (see Cheng and Greiner (1999), Comparing Bayesian network classifiers. Proceedings UAI, pp. 101-107.), instance-based algorithms, support vector machines (see e.g., Shevade et al., (1999), Improvements to SMO Algorithm for SVM Regression. Technical Report CD-99-16, Control Division Dept of Mechanical and Production Engineering, National University of Singapore; Smola et al., (1998). A Tutorial on Support Vector Regression. Neuro-COLT2 Technical Report Series—NC2-TR-1998-030; Scholkopf, (1998). SVMs—a practical consequence of learning theory. IEEE Intelligent Systems. *IEEE Intelligent Systems* 13.4: 18-21; Boser et al., (1992), A Training Algorithm for Optimal Margin Classifiers V 144-52; and Burges (1998), A tutorial on support vector machines for pattern recognition. Data Mining and Knowledge Discovery 2 (1998): 121-67), vote algorithm, cost-sensitive classifier, stacking algorithm, classification rules, and decision tree algorithms (see Witten and Frank (2005), Data Mining Practical machine learning Tools and Techniques. Morgan Kaufmann, San Francisco, Second Edition.).

Suitable association rule mining algorithms include, but are not limited to APriori algorithm (see Witten and Frank (2005), Data Mining: Practical machine learning Tools and Techniques. Morgan Kaufmann, San Francisco, Second Edition), FP-growth algorithm, association rule mining algorithms that can handle large number of features, colossal pattern mining algorithms, direct discriminative pattern mining algorithm, decision trees, rough sets (see Zdzislaw Pawlak (1992), Rough Sets Theoretical Aspects of Reasoning About Data. Kluwer Academic Print on Demand) and Self-Organizing Map (SOM) algorithm.

In an embodiment, a suitable association rule mining algorithm for handling large numbers of features include, but are not limited to, CLOSET+ (see Wang et. al (2003), CLOSET+: Searching for best strategies for mining frequent closed item sets, ACM SIGKDD 2003, pp. 236-245), CHARM (see Zaki et. al (2002), CHARM: An efficient algorithm for closed itemset mining, SIAM 2002, pp. 457-473), CARPENTER (see Pan et. al (2003), CARPENTER: Finding Closed Patterns in Long Biological Datasets, ACM SIGKDD 2003, pp. 637-642), and COBBLER (see Pan et al (2004), COBBLER: Combining Column and Row Enumeration for Closed Pattern Discovery, SSDBM 2004, pp. 21).

In an embodiment a suitable algorithm for finding direct discriminative patterns include, but are not limited to, DDPM (see Cheng et. al (2008), Direct Discriminative Pattern Mining for Effective Classification, ICDE 2008, pp. 169-178), HARMONY (see Jiyong et. al (2005), HARMONY: Efficiently Mining the Best Rules for Classification, SIAM 2005, pp. 205-216), RCBT (see Cong et. al (2005), Mining top-K covering rule groups for gene expression data, ACM SIGMOD 2005, pp. 670-681), CAR (see Kianmehr et al (2008), CARSVM: A class association rule-based classification framework and its application in gene expression data, Artificial Intelligence in Medicine 2008, pp. 7-25), and PATCLASS (see Cheng et. al (2007), Discriminative Frequent Pattern Analysis for Effective Classification, ICDE 2007, pp. 716-725).

In an embodiment a suitable algorithm for finding colossal patterns include, but are not limited to, Pattern Fusion algorithm (see Zhu et. al (2007), Mining Colossal Frequent Patterns by Core Pattern Fusion, ICDE 2007, pp. 706-715).

In an embodiment, a suitable feature evaluation algorithm is selected from the group of information gain algorithm, Relief algorithm (see e.g., Robnik-Sikonja and Kononenko (2003), Theoretical and empirical analysis of Relief and ReliefF. *Machine learning*, 53:23-69; and Kononenko (1995). On biases in estimating multi-valued attributes. In IJCAI95, pages 1034-1040), ReliefF algorithm (see e.g., Kononenko, (1994), Estimating attributes: analysis and extensions of Relief. In: L. De Raedt and F. Bergadano (eds.): *Machine learning*: ECML-94. 171-182, Springer Verlag.), RReliefF algorithm, symmetrical uncertainty algorithm, gain ratio algorithm, and ranker algorithm.

In an embodiment, a suitable machine learning algorithm is a feature subset selection algorithm selected from the group of correlation-based feature selection (CFS) algorithm (see Hall, M. A. 1999. Correlation-based feature selection for Machine Learning. Ph.D. thesis. Department of Computer Science—The University of Waikato, New Zealand.), and the wrapper algorithm in association with any other machine learning algorithm. These feature subset selection algorithms may be associated with a search method selected from the group of greedy stepwise search algorithm, best first search algorithm, exhaustive search algorithm, race search algorithm, and rank search algorithm.

In an embodiment, a suitable machine learning algorithm is a Bayesian network algorithm including the naïve Bayes algorithm.

In an embodiment, a suitable machine learning algorithm is an instance-based algorithm selected from the group of instance-based 1 (IB1) algorithm, instance-based k-nearest neighbor (IBK) algorithm, KStar, lazy Bayesian rules (LBR) algorithm, and locally weighted learning (LWL) algorithm.

In an embodiment, a suitable machine learning algorithm for classification or prediction is a support vector machine algorithm. In a preferred embodiment, a suitable machine learning algorithm is a support vector machine algorithm that uses the sequential minimal optimization (SMO) algorithm. In a preferred embodiment, the machine learning algorithm is a support vector machine algorithm that uses the sequential minimal optimization for regression (SMOReg) algorithm (see e.g., Shevade et al., (1999), Improvements to SMO Algorithm for SVM Regression. Technical Report CD-99-16, Control Division Dept of Mechanical and Production Engineering, National University of Singapore; Smola & Scholkopf (1998), A Tutorial on Support Vector Regression. NeuroCOLT2 Technical Report Series—NC2-TR-1998-030).

In an embodiment, a suitable machine learning algorithm is a self-organizing map (Self-organizing maps, Teuvo Kohonen, Springer).

In an embodiment, a suitable machine learning algorithm is a decision tree algorithm selected from the group of logistic model tree (LMT) algorithm, alternating decision tree (ADTree) algorithm (see Freund and Mason (1999), The alternating decision tree learning algorithm. Proc. Sixteenth International Conference on machine learning, Bled, Slovenia, pp. 124-133), M5P algorithm (see Quinlan (1992), Learning with continuous classes, in Proceedings AI'92, Adams & Sterling (Eds.), World Scientific, pp. 343-348; Wang and Witten (1997), Inducing Model Trees for Continuous Classes. 9th European Conference on machine learning, pp. 128-137), and REPTree algorithm (Witten and Frank, 2005).

In an embodiment, a target feature is selected from the group of a continuous target feature and a discrete target feature. A discrete target feature may be a binary target feature.

In an embodiment, at least one plant-based molecular genetic marker is from a plant population and the plant population may be an unstructured plant population. The plant population may include inbred plants or hybrid plants or a combination thereof. In an embodiment, a suitable plant population is selected from the group of maize, soybean, sorghum, wheat, sunflower, rice, canola, cotton, and millet. In an embodiment, the plant population may include between about 2 and about 100,000 members.

In an embodiment, the number of molecular genetic markers may range from about 1 to about 1,000,000 markers. The features may include molecular genetic marker data that includes, but is not limited to, one or more of a simple sequence repeat (SSR), cleaved amplified polymorphic sequences (CAPS), a simple sequence length polymorphism (SSLP), a restriction fragment length polymorphism (RFLP), a random amplified polymorphic DNA (RAPD) marker, a single nucleotide polymorphism (SNP), an arbitrary fragment length polymorphism (AFLP), an insertion, a deletion, any other type of molecular genetic marker derived from DNA, RNA, protein, or metabolite, a haplotype created from two or more of the above described molecular genetic markers derived from DNA, and a combination thereof.

In an embodiment, the features may also include one or more of a simple sequence repeat (SSR), cleaved amplified polymorphic sequences (CAPS), a simple sequence length polymorphism (SSLP), a restriction fragment length polymorphism (RFLP), a random amplified polymorphic DNA (RAPD) marker, a single nucleotide polymorphism (SNP), an arbitrary fragment length polymorphism (AFLP), an insertion, a deletion, any other type of molecular genetic marker derived from DNA, RNA, protein, or metabolite, a haplotype created from two or more of the above described molecular genetic markers derived from DNA, and a combination thereof, in conjunction with one or more phenotypic measurements, microarray data of expression levels of RNAs including mRNA, micro RNA (miRNA), non-coding RNA (ncRNA), analytical measurements, biochemical measurements, or environmental measurements or a combination thereof as features.

A suitable target feature in a plant population includes one or more numerically representable and/or quantifiable phenotypic traits including disease resistance, yield, grain yield, yarn strength, protein composition, protein content, insect resistance, grain moisture content, grain oil content, grain oil quality, drought resistance, root lodging resistance, plant height, ear height, grain protein content, grain amino acid content, grain color, and stalk lodging resistance.

In an embodiment, a genotype of the sample plant population for one or more molecular genetic markers is experimentally determined by direct DNA sequencing.

In an embodiment, a method of mining a data set with at least one plant-based molecular genetic marker to find an association rule, and utilize features created from these association rules for classification or prediction for one or more target features, wherein the method includes the steps of:
 (a) detecting association rules;
 (b) creating new features based on the findings of step (a) and adding these features to the data set;
 (c) evaluating features;
 (d) selecting a subset of features from features in the data set; and
 (e) developing a model for prediction or classification for one or more target features with at least one feature created at step (b).
 In an embodiment, a method to select inbred lines, select hybrids, rank hybrids, rank hybrids for a certain geography, select the parents of new inbred populations, find segments for introgression into elite inbred lines, or any combination thereof is completed using any combination of the steps (a)-(e) above.

In an embodiment, the detecting association rules include spatial and temporal associations using self-organizing maps.

In an embodiment, at least one feature of a model for predicting or classification is the subset of features selected earlier using a feature evaluation algorithm.

In an embodiment, cross-validation is used to compare algorithms and sets of parameter values. In an embodiment, receiver operating characteristic (ROC) curves are used to compare algorithms and sets of parameter values.

In an embodiment, one or more features are derived mathematically or computationally from other features.

In an embodiment, a method of mining a data set that includes at least one plant-based molecular genetic marker is disclosed, to find at least one association rule, and utilizing features from these association rules for classification or prediction for one or more target features, wherein the method includes the steps of:
 (a) detecting association rules;
  (i) wherein association rules, spatial and temporal associations are detected using self organizing maps.
 (b) creating new features based on the findings of step (a) and adding these features to the data set;
 (c) developing a model for prediction or classification for one or more target features with at least one feature created at step (b);
 wherein the steps (a), (b), and (c) may be preceded by the step of selecting a subset of features from features in the data set.

In an embodiment, a method of mining a data set that includes at least one plant-based molecular genetic marker to find at least one association rule and utilizing features created from these association rules for classification or prediction is disclosed, wherein the method includes the steps of:
 (a) detecting association rules;
 (b) creating new features based on the findings based on the findings of step (a) and adding these features to the data set;
 (c) selecting a subset of features in the data set.

In an embodiment wherein the results of these methods comprise a data set with at least one plant-based molecular genetic marker used to find at least one association rule and utilizing features created from these association rules for classification or prediction are applied to:
 (a) predict hybrid performance,
 (b) predict hybrid performance across various geographical locations;
 (c) select inbred lines;
 (d) select hybrids;
 (e) rank hybrids for certain geographies;
 (f) select the parents of new inbred populations;
 (g) find DNA segments for introgression into elite inbred lines;
 (h) or any combination thereof (a)-(g).

In an embodiment, a data set with at least one plant-based molecular genetic marker is used to find at least one association rule and features created from these association rules are used for classification or prediction and selecting at least one plant from the plant population for one or more target features of interest.

In an embodiment, prior knowledge, comprised of preliminary research, quantitative studies of plant genetics, gene networks, sequence analyses, or any combination of thereof, is considered.

In an embodiment, the methods described above are modified to include the following steps:
 (a) reducing dimensionality by replacing the original features with a combination of one or more of the features included in one or more of the association rules;
 (b) mining discriminative and essential frequent patterns via model-based search tree.

BRIEF DESCRIPTION OF THE DRAWINGS

FIG. 1: Area under the ROC curve, before and after adding the new features from step (b).

DETAILED DESCRIPTION

Association rule mining algorithms provide the framework and the scalability needed to find relevant interactions on very large datasets.

Methods disclosed herein are useful for identifying multi-locus interactions affecting phenotypes. Methods disclosed herein are useful for identifying interactions between molecular genetic markers, haplotypes and environmental factors. New features created based on these interactions are useful for classification or prediction The robustness of some of these methods with respect to multicollinearity problems and missing values for features, as well as the capacity of these methods to describe intricate dependencies between features, makes such methods suitable for analysis of large, complex datasets that include features based on molecular genetic markers.

WEKA (Waikato Environment for Knowledge Analysis developed at University of Waikato, New Zealand) is a suite of machine learning software, written using the Java programming language which implements numerous machine learning algorithms from various learning paradigms. This machine learning software workbench facilitates the implementation of machine learning algorithms and supports algorithm development or adaptation of data mining and computational methods. WEKA also provides tools to appropriately test the performance of each algorithm and sets of parameter values through methods such as cross-validation and ROC (Receiver Operating Characteristic) curves. WEKA was used to implement machine learning algorithms for modeling. However, one of ordinary skill in the art would appreciate that other machine learning software may be used to practice the present invention.

Moreover, data mining using the approaches described herein provides a flexible, scalable framework for modeling with datasets that include features based on molecular genetic markers. This framework is flexible because it includes tests (i.e. cross-validation and ROC curves) to determine which algorithm and specific parameter settings should be used for the analysis of a data set. This framework is scalable because it is suitable for very large datasets.

In an embodiment, methods to mine data sets containing features created from at least one plant-based molecular genetic marker to find at least one association rule and to then use features created from these association rules for classification or prediction are disclosed. Some of these methods are suitable for classification or prediction with datasets containing plant and animal features.

In an embodiment, steps to mine a data set with at least one feature created from at least one plant-based molecular genetic marker, to find at least one association rule, and utilizing features created from these association rules for classification or prediction for one or more target features include:
  (a) detecting association rules;
  (b) creating new features based on the findings of step (a) and adding these features to the data set;
  (c) model development for one or more target features with at least one feature created using the features created on step (b);
  (d) selecting a subset of features from features in the data set; and
  (e) detecting association rules from spatial and temporal associations using self-organizing maps.

In an embodiment, a method of mining a data set with one or more features is disclosed, wherein the method includes using at least one plant-based molecular marker to find at least one association rule and utilizing features created from these association rules for classification or prediction, the method comprising the steps of: (a) detecting association rules, (b) creating new features based on the findings of step (a) and adding these features to the data set; (c) selecting a subset of features from features in the data set.

In an embodiment, association rule mining algorithms are utilized for classification or prediction with one or more machine learning algorithms selected from: feature evaluation algorithms, feature subset selection algorithms, Bayesian networks, instance-based algorithms, support vector machines, vote algorithm, cost-sensitive classifier, stacking algorithm, classification rules, and decision tree algorithms.

Suitable association rule mining algorithms include, but are not limited to, APriori algorithm, FP-growth algorithm, association rule mining algorithms that can handle large number of features, colossal pattern mining algorithms, direct discriminative pattern mining algorithm, decision trees, rough sets and Self-Organizing Map (SOM) algorithm.

In an embodiment, a suitable association rule mining algorithm for handling large numbers of features include, but are not limited to, CLOSET+, CHARM, CARPENTER, and COBBLER.

In an embodiment a suitable algorithm for finding direct discriminative patterns include, but are not limited to, DDPM, HARMONY, RCBT, CAR, and PATCLASS.

In an embodiment a suitable algorithm for finding colossal patterns include, but are not limited to, Pattern Fusion algorithm.

In an embodiment, a suitable machine learning algorithm is a feature subset selection algorithm selected from the group of correlation-based feature selection (CFS) algorithm, and the wrapper algorithm in association with any other machine learning algorithm. These feature subset selection algorithms may be associated with a search method selected from the group of greedy stepwise search algorithm, best first search algorithm, exhaustive search algorithm, race search algorithm, and rank search algorithm.

In an embodiment, a suitable machine learning algorithm is a Bayesian network algorithm including the naïve Bayes algorithm.

In an embodiment, a suitable machine learning algorithm is an instance-based algorithm selected from the group of instance-based 1 (IB1) algorithm, instance-based k-nearest neighbor (IBK) algorithm, KStar, lazy Bayesian rules (LBR) algorithm, and locally weighted learning (LWL) algorithm.

In an embodiment, a suitable machine learning algorithm for classification or prediction is a support vector machine algorithm. In a preferred embodiment, a suitable machine learning algorithm is a support vector machine algorithm that uses the sequential minimal optimization (SMO) algorithm. In a preferred embodiment, the machine learning algorithm is a support vector machine algorithm that uses the sequential minimal optimization for regression (SMOReg) algorithm.

In an embodiment, a suitable machine learning algorithm is a self-organizing map.

In an embodiment, a suitable machine learning algorithm is a decision tree algorithm selected from the group of logistic model tree (LMT) algorithm, alternating decision tree (ADTree) algorithm, M5P algorithm, and REPTree algorithm.

In an embodiment, a target feature is selected from the group of a continuous target feature and a discrete target feature. A discrete target feature may be a binary target feature.

In an embodiment, at least one plant-based molecular genetic marker is from a plant population and the plant population may be an unstructured plant population. The plant population may include inbred plants or hybrid plants or a combination thereof. In an embodiment, a suitable plant population is selected from the group of maize, soybean, sorghum, wheat, sunflower, rice, canola, cotton, and millet. In an embodiment, the plant population may include between about 2 and about 100,000 members.

In an embodiment, the number of molecular genetic markers may range from about 1 to about 1,000,000 markers. The features may include molecular genetic marker data that includes, but is not limited to, one or more of a simple sequence repeat (SSR), cleaved amplified polymorphic sequences (CAPS), a simple sequence length polymorphism (SSLP), a restriction fragment length polymorphism (RFLP), a random amplified polymorphic DNA (RAPD) marker, a single nucleotide polymorphism (SNP), an arbitrary fragment length polymorphism (AFLP), an insertion, a deletion, any other type of molecular genetic marker derived from DNA, RNA, protein, or metabolite, a haplotype created from two or more of the above described molecular genetic markers derived from DNA, and a combination thereof.

In an embodiment, the features may also include one or more of a simple sequence repeat (SSR), cleaved amplified polymorphic sequences (CAPS), a simple sequence length polymorphism (SSLP), a restriction fragment length polymorphism (RFLP), a random amplified polymorphic DNA (RAPD) marker, a single nucleotide polymorphism (SNP), an arbitrary fragment length polymorphism (AFLP), an insertion, a deletion, any other type of molecular genetic marker derived from DNA, RNA, protein, or metabolite, a haplotype created from two or more of the above described molecular genetic markers derived from DNA, and a combination thereof, in conjunction with one or more phenotypic measurements, microarray data, analytical measurements, biochemical measurements, or environmental measurements or a combination thereof as features.

A suitable target feature in a plant population includes one or more numerically representable phenotypic traits including disease resistance, yield, grain yield, yarn strength, protein composition, protein content, insect resistance, grain moisture content, grain oil content, grain oil quality, drought resistance, root lodging resistance, plant height, ear height, grain protein content, grain amino acid content, grain color, and stalk lodging resistance.

In an embodiment, a genotype of the sample plant population for the one or more molecular genetic markers is experimentally determined by direct DNA sequencing.

In an embodiment, a method of mining a data set with at least one plant-based molecular genetic marker to find an association rule, and utilize features created from these association rules for classification or prediction for one or more target features, wherein the method includes the steps of:
 (a) detecting association rules;
 (b) creating new features based on the findings of step (a) and adding these features to the data set;
 (c) evaluating features;
 (d) selecting a subset of features from features in the data set; and
 (e) developing a model for prediction or classification for one or more target features with at least one feature created at step (b).

In an embodiment, a method to select inbred lines, select hybrids, rank hybrids, rank hybrids for a certain geography, select the parents of new inbred populations, find segments for introgression into elite inbred lines, or any combination thereof is completed using any combination of the steps (a)-(e) above.

In an embodiment, where the detecting association rules include spatial and temporal associations using self-organizing maps.

In an embodiment, at least one feature of a model for predicting or classification is the subset of features selected earlier using a feature evaluation algorithm.

In an embodiment, cross-validation is used to compare algorithms and sets of parameter values. In an embodiment, receiver operating characteristic (ROC) curves are used to compare algorithms and sets of parameter values.

In an embodiment, one or more features are derived mathematically or computationally from other features.

In an embodiment, a method of mining a data set that includes at least one plant-based molecular genetic marker is disclosed, to find at least one association rule, and utilizing features from these association rules for classification or prediction for one or more target features, wherein the method includes the steps of:
 (a) detecting association rules;
  (i) wherein association rules, spatial and temporal associations are detected using self organizing maps.
 (b) creating new features based on the findings of step (a) and adding these features to the data set;
 (c) developing a model for prediction or classification for one or more target features with at least one feature created at step (b);
 wherein the steps (a), (b), and (c) above may be preceded by the step of selecting a subset of features from features in the data set.

In an embodiment, a method of mining a data set that includes at least one plant-based molecular genetic marker to find at least one association rule and utilizing features created from these association rules for classification or prediction is disclosed, wherein the method includes the steps of:
 (a) detecting association rules;
 (b) creating new features based on the findings based on the findings of step (a) and adding these features to the data set;
 (c) selecting a subset of features in the data set.

In an embodiment wherein the results of these methods comprise a data set with at least one plant-based molecular genetic marker used to find at least one association rule and utilizing features created from these association rules for classification or prediction are applied to:
 (a) predict hybrid performance,
 (b) predict hybrid performance across various geographical locations;
 (c) select inbred lines;
 (d) select hybrids;
 (e) rank hybrids for certain geographies;
 (f) select the parents of new inbred populations;
 (g) find DNA segments for introgression into elite inbred lines;
 (h) or any combination thereof (a)-(g).

In an embodiment wherein a data set with at least one plant-based molecular genetic marker is used to find at least one association rule and features created from these association rules are used for classification or prediction and selecting at least one plant from the plant population for one or more target features of interest.

In an embodiment, prior knowledge, comprised of preliminary research, quantitative studies of plant genetics, gene networks, sequence analyses, or any combination of thereof, is considered.

In an embodiment, the methods described above are modified to include the following steps:

(a) reducing dimensionality by replacing the original features with a combination of one or more of the features included in one or more of the association rules;

(b) mining discriminative and essential frequent patterns via model-based search tree.

In an embodiment, feature evaluation algorithms, such as information gain, symmetrical uncertainty, and the Relief family of algorithms, are suitable algorithms. These algorithms are capable of evaluating all features together, instead of one feature at a time. Some of these algorithms are robust to biases, missing values, and collinearity problems. The Relief family of algorithms provides tools capable of accounting for deep-level interactions, but requires reduced collinearity between features in the dataset.

In an embodiment, subset selection techniques are applied through algorithms such as the CFS subset evaluator. Subset selection techniques may be used for complexity reduction by eliminating redundant, distracting features and retaining a subset capable of properly explaining the target feature. The elimination of these distracting features generally increases the performance of modeling algorithms when evaluated using methods such as cross-validation and ROC curves. Certain classes of algorithms, such as the instance-based algorithms, are known to be very sensitive to distracting features, and others such as the support vector machines are moderately affected by distracting features. Reducing complexity by generating new features based on existing features also often leads to increased predictive performance of machine learning algorithms.

In an embodiment, filter and wrapper algorithms can be used for feature subset selection. To perform feature subset selection using filters, it is usual to associate an efficient search method (e.g. greedy stepwise, best first, and race search) for finding the best subset of features (i.e. exhaustive search may not always be computationally feasible) with a merit formula (e.g. CFS subset evaluator). The CFS subset evaluator appropriately accounts for the level of redundancy within the subset while not overlooking locally predictive features. Besides complexity reduction to support modeling, machine learning-based subset selection techniques may also be used to select a subset of features that appropriately explain the target feature while having low level of redundancy between the features included in the subset. One of the purposes of subset selection approaches is reducing wastage during future data collection, manipulation and storage efforts by focusing only on the subset found to properly explain the target feature. The machine learning techniques used for complexity reduction described herein can be compared using cross-validation and ROC curves, for example. The feature subset selection algorithm with the best performance may then be selected for the final analysis. This comparison is generally performed through cross-validation and ROC curves, applied to different combinations of subset selection algorithms and modeling algorithms. To run the cross-validation during the subset selection and modeling steps, multiple computers running a parallelized version of a machine learning software (e.g. WEKA) may be used. The techniques described herein for feature subset selection use efficient search methods for finding the best subset of features (i.e. exhaustive search is not always possible).

An aspect of the modeling methods disclosed herein is that because a single algorithm may not always be the best option for modeling every data set, the framework presented herein uses cross-validation techniques, ROC curves and precision and recall to choose the best algorithm for each data set from various options within the field of machine learning. In an embodiment, several algorithms and parameter settings may be compared using cross-validation, ROC curves and precision and recall, during model development. Several machine learning algorithms are robust to multicollinearity problems (allowing modeling with large number of features), robust to missing values, and able to account for deep level interactions between features without over-fitting the data.

In an embodiment, machine learning algorithms for modeling are support vector machines, such as the SMOReg, decision trees, such as the M5P, the RepTree, and the ADTree, in addition to Bayesian networks and instance-based algorithms. Trees generated by the M5P, REPTree, and ADTree algorithm grow focusing on reducing the variance of the target feature in the subset of samples assigned to each newly created node. The M5P is usually used to handle continuous target features, the ADTree is usually used to handle binary (or binarized) target features, and the REPTree may be used to handle both continuous and discrete target features.

An aspect of the machine learning methods disclosed herein is that the algorithms used herein may not require highly structured data sets, unlike some methods based strictly on statistical techniques, which often rely on highly structured data sets. Structured experiments are often resource intensive in terms of manpower, costs, and time because the strong environmental effect in the expression of many of the most important quantitatively inherited traits in economically important plants and animals requires that such experiments be large, carefully designed, and carefully controlled. Data mining using machine learning algorithms, however, may effectively utilize existing data that was not specifically generated for this data mining purpose.

In an embodiment, the methods disclosed herein may be used for prediction of a target feature value in one or more members of a second, target plant population based on their genotype for the one or more molecular genetic markers or haplotypes associated with the trait. The values may be predicted in advance of or instead of experimentally being determined.

In an embodiment, the methods disclosed herein have a number of applications in applied breeding programs in plants (e.g., hybrid crop plants) in association or not with other statistical methods, such as BLUP (Best Linear Unbiased Prediction). For example, the methods can be used to predict the phenotypic performance of hybrid progeny, e.g., a single cross hybrid produced (either actually or in a hypothetical situation) by crossing a given pair of inbred lines of known molecular genetic marker genotype. The methods are also useful in selecting plants (e.g., inbred plants, hybrid plants, etc.) for use as parents in one or more crosses; the methods permit selection of parental plants whose offspring have the highest probability of possessing the desired phenotype.

In an embodiment, associations between at least one feature and the target feature are learned. The associations may be evaluated in a sample plant population (e.g., a breeding population). The associations are evaluated in a first plant population by training a machine learning algorithm using a data set with features that incorporate genotypes for at least one molecular genetic marker and values for the target feature in at least one member of the plant population. The values of a target feature may then be predicted on a second population using the trained machine learning algorithm and the values for at least one feature. The values may be predicted in advance of or instead of experimentally being determined.

In an embodiment, the target feature may be a quantitative trait, e.g., for which a quantitative value is provided. In another embodiment, the target feature may be a qualitative trait, e.g., for which a qualitative value is provided. The phenotypic traits that may be included in some features may be determined by a single gene or a plurality of genes.

In an embodiment, the methods may also include selecting at least one of the members of the target plant population having a desired predicted value of a target feature, and include breeding at least one selected member of the target plant population with at least one other plant (or selfing the at least one selected member, e.g., to create an inbred line).

In an embodiment, the sample plant population may include a plurality of inbreds, single cross F1 hybrids, or a combination thereof. The inbreds may be from inbred lines that are related and/or unrelated to each other, and the single cross F1 hybrids may be produced from single crosses of the inbred lines and/or one or more additional inbred lines.

In an embodiment, the members of the sample plant population include members from an existing, established breeding population (e.g., a commercial breeding population). The members of an established breeding population are usually descendents of a relatively small number of founders and are generally inter-related. The breeding population may cover a large number of generations and breeding cycles. For example, an established breeding population may span three, four, five, six, seven, eight, nine or more breeding cycles.

In an embodiment, the sample plant population need not be a breeding population. The sample population may be a sub-population of any existing plant population for which genotypic and phenotypic data are available either completely or partially. The sample plant population may include any number of members. For example, the sample plant population includes between about 2 and about 100,000 members. The sample plant population may comprise at least about 50, 100, 200, 500, 1000, 2000, 3000, 4000, 5000, or even 6000 or 10,000 or more members. The sample plant population usually exhibits variability for the target feature of interest (e.g., quantitative variability for a quantitative target feature). The sample plant population may be extracted from one or more plant cell cultures.

In an embodiment, the value of the target feature in the sample plant population is obtained by evaluating the target feature among the members of the sample plant population (e.g., quantifying a quantitative target feature among the members of the population). The phenotype may be evaluated in the members (e.g., the inbreds and/or single cross F1 hybrids) comprising the first plant population. The target feature may include any quantitative or qualitative target feature, e.g., one of agronomic or economic importance. For example, the target feature may be selected from yield, grain moisture content, grain oil content, yarn strength, plant height, ear height, disease resistance, insect resistance, drought resistance, grain protein content, test weight, visual or aesthetic appearance, and cob color. These traits, and techniques for evaluating (e.g., quantifying) them, are well known in the art.

In an embodiment, the genotype of the sample or test plant population for the set of molecular genetic markers can be determined experimentally, predicted, or a combination thereof. For example, in one class of embodiments, the genotype of each inbred present in the plant population is experimentally determined and the genotype of each single cross F1 hybrid present in the first plant population is predicted (e.g., from the experimentally determined genotypes of the two inbred parents of each single cross hybrid). Plant genotypes can be experimentally determined by any suitable technique. In an embodiment, a plurality of DNA segments from each inbred is sequenced to experimentally determine the genotype of each inbred. In an embodiment, pedigree trees and a probabilistic approach can be used to calculate genotype probabilities at different marker loci for the two inbred parents of single cross hybrids.

In an embodiment, the methods disclosed herein may be used to select plants for a selected genotype including at least one molecular genetic marker associated with the target feature.

An "allele" or "allelic variant" refers to an alternative form of a genetic locus. A single allele for each locus is inherited separately from each parent. A diploid individual is homozygous if the same allele is present twice (i.e., once on each homologous chromosome), or heterozygous if two different alleles are present.

As used herein, the term "animal" is meant to encompass non-human organisms other than plants, including, but not limited to, companion animals (i.e. pets), food animals, work animals, or zoo animals. Preferred animals include, but are not limited to, fish, cats, dogs, horses, ferrets and other Mustelids, cattle, sheep, and swine. More preferred animals include cats, dogs, horses and other companion animals, with cats, dogs and horses being even more preferred. As used herein, the term "companion animal" refers to any animal which a human regards as a pet. As used herein, a cat refers to any member of the cat family (i.e., Felidae), including domestic cats, wild cats and zoo cats. Examples of cats include, but are not limited to, domestic cats, lions, tigers, leopards, panthers, cougars, bobcats, lynx, jaguars, cheetahs, and servals. A preferred cat is a domestic cat. As used herein, a dog refers to any member of the family Canidae, including, but not limited to, domestic dogs, wild dogs, foxes, wolves, jackals, and coyotes and other members of the family Canidae. A preferred dog is a domestic dog. As used herein, a horse refers to any member of the family Equidae. An equid is a hoofed mammal and includes, but is not limited to, domestic horses and wild horses, such as, horses, asses, donkeys, and zebras. Preferred horses include domestic horses, including race horses.

The term "association", in the context of machine learning, refers to any interrelation among features, not just ones that predict a particular class or numeric value. Association includes, but it is not limited to, finding association rules, finding patterns, performing feature evaluation, performing feature subset selection, developing predictive models, and understanding interactions between features.

The term "association rules", in the context of this invention, refers to elements that co-occur frequently within the data set. It includes, but is not limited to association patterns, discriminative patterns, frequent patterns, closed patterns, and colossal patterns.

The term "binarized", in the context of machine learning, refers to a continuous or categorical feature that has been transformed to a binary feature.

A "breeding population" refers generally to a collection of plants used as parents in a breeding program. Usually, the individual plants in the breeding population are characterized both genotypically and phenotypically.

The term "data mining" refers to the identification or extraction of relationships and patterns from data using computational algorithms to reduce, model, understand, or analyze data.

The term "decision trees" refers to any type of tree-based learning algorithms, including, but not limited to, model trees, classification trees, and regression trees.

The term "feature" or "attribute" in the context of machine learning refers to one or more raw input variables, to one or more processed variables, or to one or more mathematical combinations of other variables, including raw variables and processed variables. Features may be continuous or discrete. Features may be generated through processing by any filter algorithm or any statistical method. Features may include, but are not restricted to, DNA marker data, haplotype data, phenotypic data, biochemical data, microarray data, environmental data, proteomic data, and metabolic data.

The term "feature evaluation", in the context of this invention, refers to the ranking of features or to the ranking followed by the selection of features based on their impact on the target feature.

The phrase "feature subset" refers to a group of one or more features.

A "genotype" refers to the genetic makeup of a cell or the individual plant or organism with regard to one or more molecular genetic markers or alleles.

A "haplotype" refers to a set of alleles that an individual inherited from one parent. The term haplotype may also refer to physically linked and/or unlinked molecular genetic markers (for example polymorphic sequences) associated with a target feature. A haplotype may also refer to a group of two or more molecular genetic markers that are physically linked on a chromosome.

The term "instance", in the context of machine learning, refers to an example from a data set.

The term "interaction" within the context of this invention, refers to the association between features and target features by way of dependency of one feature on another feature.

The term "learning" in the context of machine learning refers to the identification and training of suitable algorithms to accomplish tasks of interest. The term "learning" includes, but is not restricted to, association learning, classification learning, clustering, and numeric prediction.

The term "machine learning" refers to the field of the computer sciences that studies the design of computer programs able to induce patterns, regularities, or rules from past experiences to develop an appropriate response to future data, or describe the data in some meaningful way. By "machine learning" algorithms, in the context of this invention, it is meant association rule algorithms (e.g. Apriori, discriminative pattern mining, frequent pattern mining, closed pattern mining, colossal pattern mining, and self-organizing maps), feature evaluation algorithms (e.g. information gain, Relief, ReliefF, RReliefF, symmetrical uncertainty, gain ratio, and ranker), subset selection algorithms (e.g. wrapper, consistency, classifier, correlation-based feature selection (CFS)), support vector machines, Bayesian networks, classification rules, decision trees, neural networks, instance-based algorithms, other algorithms that use the herein listed algorithms (e.g. vote, stacking, cost-sensitive classifier) and any other algorithm in the field of the computer sciences that relates to inducing patterns, regularities, or rules from past experiences to develop an appropriate response to future data, or describing the data in some meaningful way.

The term "model development" refers to a process of building one or more models for data mining.

The term "molecular genetic marker" refers to any one of a simple sequence repeat (SSR), cleaved amplified polymorphic sequences (CAPS), a simple sequence length polymorphism (SSLP), a restriction fragment length polymorphism (RFLP), a random amplified polymorphic DNA (RAPD) marker, a single nucleotide polymorphism (SNP), an arbitrary fragment length polymorphism (AFLP), an insertion, a deletion, any other type of molecular marker derived from DNA, RNA, protein, or metabolite, and a combination thereof. Molecular genetic markers also refer to polynucleotide sequences used as probes.

The term "phenotypic trait" or "phenotype" refers to an observable physical or biochemical characteristics of an organism, as determined by both genetic makeup and environmental influences. Phenotype refers to the observable expression of a particular genotype.

The term "plant" includes the class of higher and lower plants including angiosperms (monocotyledonous and dicotyledonous plants), gymnosperms, ferns, and multicellular algae. It includes plants of a variety of ploidy levels, including aneuploid, polyploid, diploid, haploid and hemizygous.

The term "plant-based molecular genetic marker" refers to any one of a simple sequence repeat (SSR), cleaved amplified polymorphic sequences (CAPS), a simple sequence length polymorphism (SSLP), a restriction fragment length polymorphism (RFLP), a random amplified polymorphic DNA (RAPD) marker, a single nucleotide polymorphism (SNP), an arbitrary fragment length polymorphism (AFLP), an insertion, a deletion, any other type of molecular marker derived from plant DNA, RNA, protein, or metabolite, and a combination thereof. Molecular genetic markers also refer to polynucleotide sequences used as probes.

The term "prior knowledge", in the context of this invention, refers to any form of information that can be used to modify the performance of a machine learning algorithm. A relationship matrix, indicating the degree of relatedness between individuals, is an example of prior knowledge.

A "qualitative trait" generally refers to a feature that is controlled by one or a few genes and is discrete in nature. Examples of qualitative traits include flower color, cob color, and disease resistance.

A "quantitative trait" generally refers to a feature that can be quantified. A quantitative trait typically exhibits continuous variation between individuals of a population. A quantitative trait is often the result of a genetic locus interacting with the environment or of multiple genetic loci interacting with each other and/or with the environment. Examples of quantitative traits include grain yield, protein content, and yarn strength.

The term "ranking" in relation to the features refers to an orderly arrangement of the features, e.g., molecular genetic markers may be ranked by their predictive ability in relation to a trait.

The term "self-organizing map" refers to an unsupervised learning technique often used for visualization and analysis of high-dimensional data.

The term "supervised", in the context of machine learning, refers to methods that operate under supervision by being provided with the actual outcome for each of the training instances.

The term "support vector machine", in the context of machine learning includes, but is not limited to, support vector classifier, used for classification purposes, and support vector regression, used for numeric prediction. Other algorithms (e.g. sequential minimal optimization (SMO)), may be implemented for training a support vector machine.

The term "target feature" in the context of this invention, refers, but is not limited to, a feature which is of interest to predict, or explain, or with which it is of interest to develop associations. A data mining effort may include one target feature or more than one target feature and the term "target feature" may refer to one or more than one feature. "Target features" may include, but are not restricted to, DNA marker data, phenotypic data, biochemical data, microarray data, environmental data, proteomic data, and metabolic data. In the field of machine learning, when the "target feature" is discrete, it is often called "class". Grain yield is an example of a target feature.

The term "unsupervised," in the context of machine learning, refers to methods that operate without supervision by not being provided with the actual outcome for each of the training instances.

Overview of Theoretical and Practical Aspects of Some Relevant Methods Association Rule Mining:

Association rule mining (ARM) is a technique for extracting meaningful association patterns among features. One of the machine learning algorithms suitable for learning association rules is the APriori algorithm.

A usual primary step of ARM algorithms is to find a set of items or features that are most frequent among all the observations. These are known as frequent itemsets. Their frequency is also known as support (the user may identify a minimum support threshold for a itemset to be considered frequent). Once the frequent itemsets are obtained, rules are extracted from them (with a user specified minimum confidence measure, for example). The later part is not as computationally intensive as the former. Hence, an objective of ARM algorithms is focused on finding frequent itemsets.

It is not always certain that the frequent itemsets are the core (most relevant) information patterns of the dataset, as there often is a lot of redundancy among patterns. As a result, many applications rely on obtaining frequent closed patterns. A frequent closed pattern is a pattern that meets the minimal support requirement specified by the user and does not have the same support as its immediate supersets. A frequent pattern is not closed if at least one of its immediate supersets has the same support count as it does. Finding frequent closed patterns allows us to find a subset of relevant interactions among the features.

The Apriori algorithm works iteratively by combining frequent itemsets with n−1 features to form a frequent itemset with n features. This procedure is exponential in execution time with the increase in number of features. Hence, extracting frequent itemsets with the Apriori algorithm becomes computationally intensive for datasets with very large number of features.

The scalability problem for finding frequent closed itemsets can be handled by some existing algorithms. CARPENTER, a depth-first row enumeration algorithm, is capable of finding frequent closed patterns from large biological datasets with large number of features. CARPENTER does not scale well with the increase in number of samples.

Other frequent pattern mining algorithms are CHARM, CLOSET. Both of them are efficient depth-first column enumeration algorithms.

COBBLER is a column and row enumeration algorithm that scale well with the increase in number of features and samples.

For many different purposes, finding discriminative frequent patterns is even more useful than finding frequent closed association patterns. Several algorithms effectively mine only discriminative patterns from the dataset. Most of the existing algorithms perform a two set approach for finding discriminative patterns: (a) Find frequent patterns (b) From the frequent patterns, obtain discriminative patterns. Step (a) is a very time consuming process and results into many redundant frequent patterns.

DDPMine (Direct Discriminative Pattern Mining), discriminative pattern mining algorithm, does not follow the above described two step approach. Instead of deriving frequent patterns, it generates a shrinked FP-tree representation of the data. This procedure, not only reduces the problem size, but also speeds up the mining process. It uses information gain as a measure to mine the discriminative patterns.

Other discriminative pattern mining algorithms are HARMONY, RCBT and PatClass. HARMONY is an instance-centric rule-based classifier. It directly mines a final set of classification rules. The RCBT classifier works by first identifying top-k covering rule groups for each row and use them for the classification framework. PatClass takes a two step procedure by first mining a set of frequent itemsets followed by a feature selection step.

Most of the existing association rule mining algorithms return small sized frequent or closed patterns. With the increase in number of features, the number of large sized frequent or closed patterns also increases. It is computationally too expensive, rather impossible, to derive all the frequent patterns of all lengths for data sets with large number of features. The Pattern fusion algorithm tries to address this problem by combining small frequent patterns into colossal patterns by taking leaps in the pattern search space.

Self-Organizing Maps:

The Self-Organizing Map (SOM) also known as Kohonen network preserving map is an unsupervised learning technique often used for visualization and analysis of high-dimensional data. Typical applications are focused on the visualization of the central dependencies within the data on the map. Some areas where they have been used include automatic speech recognition, clinical voice analysis, classification of satellite images, analyses of electrical signals from the brain, and organization and retrieval from large document collections.

The map generated by SOMs has been used to speed up the identification of association rules by methods like Apriori, by utilizing the SOM clusters (visual clusters identified during SOM training).

The SOM map consists of a grid of processing units, "neurons". Each neuron is associated with a feature vector (observation). The map attempts to represent all the available observations with optimal accuracy using a restricted set of models. At the same time the models become ordered on the grid so that similar models are close to each other and dissimilar models far from each other. This procedure enables the identification as well as the visualization of dependencies or associations between the features in the data.

During the training phase of SOM, a competitive learning algorithm is used to fit the model vectors to the grid of neurons. It is a sequential regression process, where $t=1, 2, \ldots$ is the step index: For each sample $x(t)$, first the winner index c (best matching neuron) is identified by the condition $$\forall i, \|x(t) - m_c(t)\| \leq \|x(t) - m_i(t)\|$$

After that, all model vectors or a subset of them that belong to nodes centered around node c=c(x) are updated as $$m_i(t+1)=m_i(t)+h_{c(x),i}(x(t)-m_i(t))$$

Where:
$m_c$ is the mean weight vector of the $c^{th}$ (i.e. winner) node.
$m_i$ is the mean weight vector of the $i^{th}$ node.
$h_{c(x),i}$ is the "neighborhood function", a decreasing function of the distance between the $i^{th}$ and $c^{th}$ nodes on the map grid.
$m_i(t+1)$ is the updated weight vector after the $t^{th}$ step.
This regression is usually reiterated over the available observations.

SOM algorithms have also been frequently used to explore the spatial and temporal relationships between entities. Relationships and associations between observations are derived based on the spatial clustering of these observations on the map. If the neurons represent various time states then the map visualizes the temporal patterns between observations.

Feature Evaluation:

One of the main purposes of feature evaluation algorithms is to understand the underlying process that generates the data. These methods are also frequently applied to reduce the number of "distracting" features with the aim of improving the performance of classification algorithms (see Guyon and Elisseeff (2003). An Introduction to Variable and Feature Selection. *Journal of Machine learning Research* 3, 1157-1182). The term "variable" is sometimes used instead of the broader terms "feature" or "attribute". Feature (or attribute) selection refers to the selection of variables processed through methods such as kernel methods, but is sometimes used to refer to the selection of raw input variables. The desired output of these feature evaluation algorithms is usually the ranking of features based on their impact on the target feature or the ranking followed by selection of features. This impact may be measured in different ways.

Information gain is one of the machine learning methods suitable for feature evaluation. The definition of information gain requires the definition of entropy, which is a measure of impurity in a collection of training instances. The reduction in entropy of the target feature that occurs by knowing the values of a certain feature is called information gain. Information gain may be used as a parameter to determine the effectiveness of a feature in explaining the target feature.

Symmetrical uncertainty, used by the Correlation based Feature Selection (CFS) algorithm described herein, compensates for information gain's bias towards features with more values by normalizing features to a [0,1] range. Symmetrical uncertainty always lies between 0 and 1. It is one way to measure the correlation between two nominal features.

The Ranker algorithm may also be used to rank the features by their individual evaluations at each fold of cross-validation and output the average merit and rank for each feature.

Relief is a class of attribute evaluator algorithms that may be used for the feature evaluation step disclosed herein. This class contains algorithms that are capable of dealing with categorical or continuous target features. This broad range makes them useful for several data mining applications.

The original Relief algorithm has several versions and extensions. For example, the ReliefF, an extension of the original Relief algorithm, is not limited to two class problems and can handle incomplete data sets. ReliefF is also more robust than Relief and can deal with noisy data.

Usually, in Relief and ReliefF, the estimated importance of a feature is determined by a sum of scores assigned to it for each one of the instances. Each score depends on how important the feature is in determining the class of an instance. The feature gets maximum value if it is decisive in determining the class. When a significant number of uninformative features are added to the analysis, many instances are necessary for these algorithms to converge to the correct estimates of the worth of each feature. When dealing with several neighboring misses, the important features are those for which a minimal change in their value leads to a change in the class of the instance being evaluated. In ReliefF, when the number of instances is enormous, the near hits play a minimal role and the near misses play a huge role, but with problems of practical size near hits play a bigger role.

RReliefF is an extension of ReliefF that deals with continuous target features. The positive updates form the probabilities that the feature discriminates between the instances with different class values. On the other hand, the negative updates form the probabilities that the feature discriminates between the instances with the same class values. In regression problems, it is often difficult to infer whether two instances pertain to the same class or not, therefore the algorithm introduces a probability value that predicts if the values of two instances are different. Therefore, RReliefF algorithms reward features for not separating similar prediction values and punish features for not separating different prediction values. RReliefF, differently from Relief and ReliefF, does not use signs, so the concept of hit and miss does not apply. RReliefF considers good features to be the ones that separate instances with different prediction values and do not separate instances with close prediction values.

The estimations generated by algorithms from the class of Relief algorithms are dependent on the number of neighbors used. If one does not use a restriction on the number of neighbors, each feature will suffer the impact of all of the samples in the data set. The restriction on the number of samples used provides estimates by Relief algorithms that are averages over local estimates in smaller parts of the instance space. These local predictions allow Relief algorithms to take into account other features when updating the weight of each feature, as the nearest-neighbors are determined by a distance measure that considers all of the features. Therefore, Relief algorithms are sensitive to the number and usefulness of the features included in the data set. Other features are considered through their conditional dependencies to the feature being updated given the predicted values, which can be detected in the context of locality. The distance between instances is determined by the sum of the differences in the values of the "relevant" and "irrelevant" features. As other k-nearest-neighbor algorithms, these algorithms are not robust to irrelevant features. Therefore, in the presence of a lot of irrelevant features, it is recommended to use a large value of k (i.e. increase number of nearest-neighbors). Doing that, better conditions are provided for the relevant features to "impose" the "correct" update for each feature. However, it is known that Relief algorithms can lose functionality when the number of nearest-neighbors used in the weight formula is too big, often confounding informative features. This is especially true when all of the samples are considered as there will be only a small asymmetry between hits and misses and this asymmetry is much more prominent when only a few nearest-neighbors are considered. The power of Relief algorithms comes from the ability to use the context of locality while providing a global view.

RReliefF algorithm may tend to underestimate important numerical features in comparison to nominal features when calculating Euclidian or Manhattan distance between instances to determine nearest-neighbors. RReliefF also overestimates random (non-important) numerical features, potentially reducing the separability of two groups of features. The ramp function (see Hong (1994) Use of contextual information for feature ranking and discretization. Technical Report RC19664, IBM; and Hong (1997) IEEE transactions on knowledge and data engineering, 9(5) 718-730) can be used to overcome this problem of RReliefF.

When evaluating the weight that should be assigned to each feature in a given feature set, it is standard practice to emphasize closer instances in comparison to more distant instances. It is often dangerous, however, to use too small a number of neighbors with noisy and complex target features since this can lead to a loss of robustness. Using a larger number of nearest-neighbors avoids reducing the importance of some features for which the top 10 (for example) nearest-neighbors are temporally similar. Such features lose importance as the number of neighbors decreases. If the influence of all neighbors is treated as equal (disregarding their distance to the query point), then the proposed value for the number of nearest-neighbors is usually 10. If distance is taken into account, the proposed value is usually 70 nearest-neighbors with exponentially decreasing influence.

ReliefF and RReliefF are context sensitive and therefore more sensitive to the number of random (non important) features in the analysis than myopic measures (e.g. gain ratio and MSE). Relief algorithms estimate each feature in the context of other features and better features get higher scores. Relief algorithms tend to underestimate less important features when there are hundreds of important features in the data set yet duplicated or highly redundant features will share the credit and seem to be more important than they actually are. This can occur because additional copies of the feature change the problem space in which the nearest-neighbors are searched. Using nearest-neighbors, the updates will only occur when there are differences between feature values for two neighboring instances. Therefore, no updates for a given feature at a given set of neighbors will occur if the difference between two neighbors is zero. Highly redundant features will have these differences always equal to zero, reducing the opportunity for updating across all neighboring instances and features. Myopic estimators such as Gain ratio and MSE are not sensitive to duplicated features. However, Relief algorithms will perform better than myopic algorithms if there are interactions between features.

Subset Selection

Subset selection algorithms rely on a combination of an evaluation method (e.g. symmetrical uncertainty, and information gain) and a search method (e.g. ranker, exhaustive search, best first, and greedy hill-climbing).

Subset selection algorithms, similarly to feature evaluation algorithms, rank subsets of features. In contrast to feature evaluation algorithms, however, subset selection algorithms aim at selecting the subset of features with the highest impact on the target feature, while accounting for the degree of redundancy between the features included in the subset. Subset selection algorithms are designed to be robust to multicollinearity and missing values and thus allow for selection from an initial pool of hundreds or even thousands of features. The benefits from feature subset selection include facilitating data visualization and understanding, reducing measurement and storage requirements, reducing training and utilization times, and eliminating distracting features to improve classification. For example, the results from subset selection methods are useful for plant and animal geneticists because they can be used to pre-select the molecular genetic markers to be analyzed during a marker assisted selection project with a phenotypic trait as the target feature. This can significantly reduce the number of molecular genetic markers that must be assayed and thus reduce the costs associated with the effort.

Subset selection algorithms can be applied to a wide range of data sets. An important consideration in the selection of a suitable search algorithm is the number of features in the data set. As the number of features increases, the number of possible subsets of features increases exponentially. For this reason, the exhaustive search algorithm is only suitable when the number of features is relatively small. With adequate computational power, however, it is possible to use exhaustive search to determine the most relevant subset of features.

There are several algorithms suitable for data sets with a feature set that is too large (or the computational power available is not large enough) for exhaustive search. Two basic approaches to subset selection algorithms are the process of adding features to a working subset (forward selection) and deleting from the current subset of features (backward elimination). In machine learning, forward selection is done differently than the statistical procedure with the same name. Here, the feature to be added to the current subset is found by evaluating the performance of the current subset augmented by one new feature using cross-validation. In forward selection, subsets are built up by adding each remaining feature in turn to the current subset while evaluating the expected performance of each new subset using cross-validation. The feature that leads to the best performance when added to the current subset is retained and the process continues. The search ends when none of the remaining available features improves the predictive ability of the current subset. This process finds a local (i.e. not necessarily global) optimum set of features.

Backward elimination is implemented in a similar fashion. With backward elimination, the search ends when further reduction in the feature set does not improve the predictive ability of the subset. To introduce bias towards smaller subsets one may require the predictive ability to improve by a certain amount for a feature to be added (during forward selection) or deleted (during backward elimination).

In an aspect, the best first algorithm can search forward, backward or in both directions (by considering all possible single feature additions and deletions at a given point) through the application of greedy hill-climbing augmented with a backtracking facility (see Pearl, J. (1984), Heuristics: Intelligent Search Strategies for Computer Problem Solving. Addison-Wesley, p. 48; and Russell, S. J., & Norvig, P. Artificial Intelligence: A Modern Approach. 2nd edition. Pearson Education, Inc., 2003, pp. 94 and 95). This method keeps a list with all of the subsets previously visited and revisits them whenever the predictive ability stops to improve for a certain subset. It will search the entire space (i.e. exhaustive search) if time is permitted and no stop criterion is imposed, being much less likely to find a local maximum when compared to forward selection and backward elimination. Best first results are, as expected, very similar to the results obtained with exhaustive search. In an aspect, the beam search method works similarly to best first but truncates the list of feature subsets at each stage, so it is restricted to a fixed number called the beam width.

In an aspect, the genetic algorithm is a search method that uses random perturbations of a current list of candidate subsets to generate new good subsets (see Schmitt, Lothar M (2001), Theory of Genetic Algorithms, Theoretical Computer Science (259), pp. 1-61). They are adaptive and use search techniques based on the principles of natural selection in biology. Competing solutions are set up and evolve over time searching the solution space in parallel (which helps with avoiding local maxima). Crossover and mutations are applied to the members of the current generation to create the next generation. The random addition or deletion of features from a subset is conceptually analogous to the role of mutation in natural systems. Similarly, crossovers combine features from a pair of subsets to form a new subset. The concept of fitness comes into play in that the fittest (best) subset at a given generation has a greater chance of being selected to form a new subset through crossover and mutation. Therefore, good subsets evolve over time.

In an aspect, the scheme-specific (wrapper) (Kohavi and John (1997), Wrappers for feature selection. *Artificial Intelligence*, 97(1-2):273-324, December 1997.) is a suitable search method. The idea here is to select the subset of features that will have the best classification performance when used for building a model with a specific algorithm. Accuracy is evaluated through cross-validation, holdout set, or bootstrap estimator. A model and a set of cross-validation folds must be performed for each subset of features being evaluated. For example, forward selection or backward elimination with k features and 10-fold cross-validation will take approximately $k^2$ times 10 learning procedures. Exhaustive search algorithms will take something on the order of $2^k$ times 10 learning procedures. Good results were shown for scheme-specific search, with the backward elimination leading to more accurate models than forward selection, and also larger subsets. More sophisticated techniques are not usually justified but can lead to much better results in some cases. Statistical significance tests can be used to determine the time to stop searching based on the chances that a subset being evaluated will lead to improvement over the current best subset.

In an aspect, race search that uses a t-test to determine the probability of a subset being better than the current best subset by at least a small user-specified threshold is suitable. If during the leave-one-out cross-validation process, the probability becomes small, a subset can be discarded because it is very unlikely that adding or deleting features to this subset will lead to an improvement over the current best subset. In forward selection, for example, all of the feature additions to a subset are evaluated simultaneously and the ones that don't perform well enough are dropped. Therefore, not all the instances are used (on leave-one-out cross-validation) to evaluate all the subsets. The race search algorithm also blocks all of the nearly identical feature subsets and uses Bayesian statistics to maintain a probability distribution on the estimate of the mean leave-one-out cross-validation error for each competing subset. Forward selection is used but, instead of sequentially trying all the possible changes to the best subset, these changes are raced and the race finishes when cross-validation finishes or a single subset is left.

In an aspect, schemata search is a more complicated method designed for racing, running an iterative series of races that each determines if a feature should be included or not (see Moore, A. W., and Lee, M. S. (1994). Efficient algorithms for minimizing cross-validation error. In Cohen, W. W., and Hirsh, H., eds., Machine learning: Proceedings of the Eleventh International Conference. Morgan Kaufmann). A search begins with all features marked as unknown rather than an empty or full set of features. All combinations of unknown features are used with equal probability. In each round, a feature is chosen and subsets with and without the chosen feature are raced. The other features that compose the subset are included or excluded randomly at each point in the evaluation. The winner of a race is used as starting point for the next iteration of races. Given the probabilistic framework, a good feature will be included in the final subset even if it depends on another feature. Schemata search takes interacting features into account while speeding up the search process and has been shown to be more effective and much faster than race search (which uses forward or backward selection).

In an aspect, rank race search orders the features based on their information gain, for example, and then races using subsets that are based on the rankings of the features. The race starts with no features, continues with the top-ranked feature, the top two features, the top three features, and so on. Cross-validation may be used to determine the best search method for a specific data set.

In an aspect, selective naïve Bayes uses a search algorithm such as forward selection to avoid including redundant features and features that are dependent on each other (see eg., Domingos, Pedro & Michael Pazzani (1997) "On the optimality of the simple Bayesian classifier under zero-one loss". Machine learning, 29:103-137). The best subset is found by simply testing the performance of the subsets using the training set.

Filter methods operate independently of any learning algorithm, while wrapper methods rely on a specific learning algorithm and use methods such as cross-validation to estimate the accuracy of feature subsets. Wrappers often perform better than filters, but are much slower, and must be re-run whenever a different learning algorithm is used or even when a different set of parameter settings is used. The performance of wrapper methods depend on which learning algorithm is used, the procedure used to estimate the off-sample accuracy of the learning algorithm, and the organization of the search.

Filters (e.g. the CFS algorithm) are much faster than wrappers for subset selection (due to the reasons pointed out above), so filters can be used with larger data sets. Filters can also improve the accuracy of a certain algorithm by providing a starting feature subset for the wrapper algorithms. This process would therefore speed up the wrapper analysis.

The original version of the CFS algorithm, measured only the correlation between discrete features, so it would first discretize all the continuous features. More recent versions handle continuous features without need for discretization.

CFS assumes that the features are independent given the target feature. If strong feature dependency exists, CFS' performance may suffer and it might fail to select all of the relevant features. CFS is effective at eliminating redundant and irrelevant features and will detect all of the relevant features in the absence of strong dependency between features. CFS will accept features capable of predicting the response variable in areas of the instance space not already predicted by other features.

There are variations of CFS capable of improving detection of locally predictive features, very important in cases where strong globally predictive features overshadow locally predictive ones. CFS has been shown to outperform wrappers much of the time (Hall, M. A. 1999. Correlation-based feature selection for Machine Learning. Ph.D. thesis. Department of Computer Science—The University of Waikato, New Zealand.), especially with small data sets and in cases where there are small feature dependencies.

In the case of the CFS algorithm, the numerator of the evaluation function indicates how predictive of the target feature the subset is, and the denominator indicates how redundant the features in the subset are. In the original CFS algorithm, the target feature is first made discrete using the method of Fayyad and Irani (Fayyad, U. M. and Irani, K. B. 1993. Multi-interval discretisation of continuous-valued attributes for classification learning. In Proceedings of the Thirteenth International Join Conference on Artificial Intelligence. Morgan Kaufmann, 1993.). The algorithm then calculates all feature-target feature correlations (that will be used in the numerator of the evaluation function) and all feature-feature correlations (that will be used in the denominator of the evaluation function). After that, the algorithm searches the feature subset space (using any user-determined search method) looking for the best subset. In a modification of the CFS algorithm, symmetrical uncertainty is used to calculate correlations.

The greatest assumption of CFS is that the features are independent given the target feature (i.e. that there are no interactions). Therefore, if strong interactions are present, CFS may fail to detect relevant features. CFS is expected to perform well under moderate levels of interaction. CFS tends to penalize noisy features. CFS is heavily biased towards small feature subsets, leading to reduced accuracy in some cases. CFS is not heavily dependent on the search method used. CFS may be set to place more value on locally predictive features, even if these features don't show outstanding global predictive ability. If not set to account for locally predictive features, the bias of CFS towards small subsets may exclude these features. CFS tends to do better than wrappers in small data sets also because it does not need so save part of the data set for testing. Wrappers perform better than CFS when interactions are present. A wrapper with forward selection can be used to detect pairwise interactions, but backward elimination is needed to detect higher level interactions. Backward searches, however, make wrappers even slower. Bi-directional search can be used for wrappers, starting from the subset chosen by the CFS algorithm. This smart approach can significantly reduce the amount of time needed by the wrapper to complete the search.

Model Development

For modeling of large data sets, several algorithms may be used, depending on the nature of the data. In an aspect, for example, Bayesian network methods provide useful and flexible probabilistic approach to inference.

In an aspect, the Bayes optimal classifier algorithm does more than apply the maximum a posteriori hypothesis to a new record in order to predict the probability of its classification (Friedman et al., (1997), Bayesian network classifiers. *Machine learning*, 29:131-163). It also considers the probabilities from each of the other hypotheses obtained from the training set (not just the maximum a posteriori hypothesis) and uses these probabilities as weighting factors for future predictions. Therefore, future predictions are carried out using all of the hypotheses (i.e., all of the possible models) weighted by their posterior probabilities.

In an aspect, the naïve Bayes classifier assigns the most probable classification to a record, given the joint probability of the features. Calculating the joint probability requires a large data set and is computationally intensive. The naïve Bayes classifier is part of a larger class of algorithms called Bayesian networks. Some of these Bayesian networks can relax the strong assumption made by the naïve Bayes algorithm of independence between features. A Bayesian network is a direct acyclic graph (DAG) with a conditional probability distribution for each node. It relies on the assumption that features are conditionally independent given the target feature (naïve Bayes) or its parents, which may require the inclusion of the target feature (Bayesian augmented network) or not (general Bayesian network). The assumption of conditional independence is restricted to subsets of the features, and this leads to a set of conditional independence assumptions, together with a set of conditional probabilities. The output reflects a description of the joint probability for a set of features.

In an aspect, different search algorithms can be implemented using the package WEKA in each of these areas, and probability tables may be calculated by the simple estimator or by Bayesian model averaging (BMA).

Regarding methods to search for the best network structure, one option is to use the global score metric-based algorithms. These algorithms rely on cross-validation performed with leave-one-out, k-fold, or cumulative cross-validation. The leave-one-out method isolates one record, trains on the rest of the data set, and evaluates that isolated record (repeatedly, for each of the records). The k-fold method splits the data into k parts, isolates one of these parts, trains with the rest of the data set, and evaluates the isolated set of records. The cumulative cross-validation algorithm starts with an empty data set and adds record by record, updating the state of the network after each additional record, and evaluating the next record to be added according to the current state of the network.

In an aspect, an appropriate network structure found by one of these processes is considered as the structure that best fits the data, as determined by a global or a local score. It can also be considered as a structure that best encodes the conditional independencies between features; these independencies can be measured by Chi-squared tests or mutual information tests. Conditional independencies between the features are used to build the network. When the computational complexity is high, the classification may be performed by a subset of the features, determined by any subset selection method.

In an alternative approach to building the network, the target feature may be used as any other node (general Bayesian network) when finding dependencies, after that it is isolated from other features via its Markov blanket. The Markov blanket isolates a node from being affected by any node outside its boundary, which is composed of the node's parents, its children, and the parents of its children. When applied, the Markov blanket of the target feature is often sufficient to perform classification without a loss of accuracy and all of the other nodes may be deleted. This method selects the features (i.e. the ones included in the Markov blanket) that should be used in the classification and reduces the risk of over-fitting the data by deleting all nodes that are outside the Markov blanket of the target feature.

In an aspect, instance-based algorithms are also suitable for model development. Instance-based algorithms, also referred to as "lazy" algorithms, are characterized by generating a new model for each instance, instead of basing predictions on trees or networks generated (once) from a training set. In other words, they do not provide a general function that can explain the target feature. These algorithms store the entire training set in memory and build a model from a set of records similar to those being tested. This similarity is evaluated through nearest-neighbor or locally weighted methods, using Euclidian distances. Once a set of records is selected, the final model may be built using several different algorithms, such as the naïve Bayes. The resulting model is generally not designed to perform well when applied to other records. Because the training observations are stored explicitly, not in the form of a tree or network, information is never wasted when training instance-based algorithms.

In an aspect, instance-based algorithms are useful for complex, multi-dimensional problems for which the computational demands of trees and networks exceed the available memory. This approach avoids the problem of attempting to perform complexity reduction via selection of features to fit the demands of trees or networks. However, this process may perform poorly when classifying a new instance, because all of the computations take place at the classification time. This is generally not a problem during applications in which one or a few instances are to be classified at a time. Usually, these algorithms give similar importance to all of the features, without placing more weight on those that better explain the target feature. This may lead to selection of instances that are not actually closest to the instance being evaluated in terms of their relationship to the target feature. Instance-based algorithms are robust to noise in data collection because instances get the most common assignment among their neighbors or an average (continuous case) of these neighbors, and these algorithms usually perform well with very large training sets.

In an aspect, support vector machines (SVMs) are used to model data sets for data mining purposes. Support vector machines are an outgrowth of Statistical Learning Theory and were first described in 1992. An important aspect of SVMs is that once the support vectors have been identified, the remaining observations can be removed from the calculations, thus greatly reducing the computational complexity of the problem.

In an aspect, decision tree learning algorithms are suitable machine learning methods for modeling. These decision tree algorithms include ID3, Assistant, and C4.5. These algorithms have the advantage of searching through a large hypothesis space without many restrictions. They are often biased towards building small trees, a property that is sometimes desirable.

The resulting trees can usually be represented by a set of "if-then" rules; this property which does not apply to other classes of algorithms such as instance-based algorithms, can improve human readability. The classification of an instance occurs by scanning the tree from top to bottom and evaluating some feature at each node of the tree. Different decision tree learning algorithms vary in terms of their capabilities and requirements; some work only with discrete features. Most decision tree algorithms also require the target feature to be binary while others can handle continuous target features. These algorithms are usually robust to errors in the determination of classes (coding) for each feature. Another relevant feature is that some of these algorithms can effectively handle missing values.

In an aspect, the Iterative Dichotomiser 3 (ID3) algorithm is a suitable decision tree algorithm. This algorithm uses "information gain" to decide which feature best explains the target by itself, and it places this feature in the top of the tree (i.e., at the root node). Next, a descendant is assigned for each class of the root node by sorting the training records according to classes of the root node and finding the feature with the greatest information gain in each of these classes. This cycle is repeated for each newly added feature, and so on. This algorithm can not "back-track" to reconsider its previous decisions, and this may lead to convergence to a local maximum. There are several extensions of the ID3 algorithm that perform "post-pruning" of the decision tree, which is a form of back-tracking.

The ID3 algorithm performs a "hill-climbing search" through the space of decision trees, starting from a simple hypothesis and progressing through more elaborate hypotheses. Because it performs a complete search of the hypothesis space, it avoids the problem of choosing a hypothesis space that does not contain the target feature. The ID3 algorithm outputs just one tree, not all reasonable trees.

Inductive bias can occur with the ID3 algorithm because it is a top-down, breadth-first algorithm. In other words, it considers all possible trees at a certain depth, chooses the best one, and then moves to the next depth. It prefers short trees over long trees, and by selecting the shortest tree at a certain depth it places features with highest information gain closest to the root.

In an aspect of decision trees, a variation of ID3 algorithm is the logistic model tree (LMT) (Landwehr et al., (2003), Logistic Model Trees. Proceedings of the 14th European Conference on machine learning. Cavtat-Dubrovnik, Croatia. Springer-Verlag.). This classifier implements logistic regression functions at the leaves. This algorithm deals with discrete target features, and can handle missing values.

The C4.5 is a decision tree generating algorithm based on the ID3 algorithm (Quinlan (1993) C4.5: Programs for machine learning. Morgan Kaufmann Publishers). Some of the improvements include, for example, choosing an appropriate feature evaluation measure; handling training data with missing feature values; handling features with differing costs; and handling continuous features.

A useful tool for evaluating the performance of binary classifiers is the Receiver Operating Characteristic (ROC) curve. The ROC curve is a graphical plot of the sensitivity vs. (1—specificity) for a binary classifier system as its discrimination threshold is varied (T. Fawcett (2003). ROC graphs: Notes and practical considerations for data mining researchers. Tech report HPL-2003-4. HP Laboratories, Palo Alto, Calif., USA). Receiver operating characteristic (ROC) curves are, therefore, constructed by plotting the 'sensitivity' against '1—specificity' for different thresholds. These thresholds determine if a record is classified as positive or negative and influence the sensitivity and the '1—specificity'. As an example, consider an analysis in which a series of plant varieties are being evaluated for their response to a pathogen and it is desirable to establish a threshold above which a variety will be considered as susceptible. The ROC curve is built over several such thresholds, which help determining the best threshold for a given problem (the one that gives the best balance between the true positive rate and the false positive rate). Lower thresholds lead to higher false positive rates because of the increased ratio of false positives and true negatives (several of the negative records are going to be assigned as positive). The area under the ROC curve is a measure of the overall performance of a classifier, but the choice of the best classifier may be based on specific sections of that curve.

Cross-validation techniques are methods by which a particular algorithm or a particular set of algorithms are chosen to provide optimal performance for a given data set. Cross-validation techniques are used herein to select a particular machine learning algorithm during model development, for example. When several algorithms are available for implementation, it is usually interesting to choose the one that is expected to have the best performance in the future. Cross-validation is usually the methodology of choice for this task.

Cross-validation is based on first separating part of the training data, then training with the rest of the data, and finally evaluating the performance of the algorithm on the separated data set. Cross-validation techniques are preferred over residual evaluation because residual evaluation is not informative as to how an algorithm will perform when applied to a new data set.

In an aspect, one variant of cross-validation, the holdout method, is based on splitting the data in two, training on the first subset, and testing on the second subset. It takes about the same amount of time to compute as the residual method, and it is preferred when the data set is large enough. The performance of this method may vary depending on how the data set is split into subsets.

In an aspect of cross-validation, a k-fold cross-validation method is an improvement over the holdout method. The data set is divided into k subsets, and the holdout method is repeated k times. The average error across the k trials is then computed. Each record is part of the testing set once, and is part of the training set k−1 times. This method is less sensitive to the way in which the data set is divided, but the computational cost is k times greater than with the holdout method.

In another aspect of cross-validation, the leave-one-out cross-validation method is similar to k-fold cross-validation. The training is performed using N−1 records (where N is the total number of records), and the testing is performed using only one record at a time. Locally weighted learners reduce the running time of these algorithms to levels similar to that of residual evaluation.

In an aspect of cross-validation, the random sample technique is another option for testing, in which a reasonably sized sample from the data set (e.g., more than 30), is used for testing, with the rest of the data set being used for training. The advantage of using random samples for testing is that sampling can be repeated any number of times, which may result in a reduction of the confidence interval of the predictions. Cross-validation techniques, however, have the advantage that records in the testing sets are independent across testing sets.

Some of the association rule algorithms described herein may be used to detect interactions among the features in a data set, and may also be used for model development. The M5P algorithm is a model tree algorithm suitable for continuous and discrete target features. It builds decision trees with regression functions instead of terminal class values. Continuous features may be directly handled without transformation to discrete features. It uses conditional class probability function to deal with discrete classes. The class whose model tree generates the greatest approximate probability value is chosen as the predicted class. The M5P algorithm represents any piecewise linear approximation to an unknown function. M5P examines all possible tests and chooses the one that maximizes the expected error reduction. Then M5P prunes this tree back by replacing sub-trees with linear regression models wherever the latter has lower estimated error. Estimated error is the average absolute difference between predicted and actual values for all the instances at a node.

During pruning, the underestimation of the error for unseen cases is compensated by $(n+v)/(n-v)$ where n is the number of instances reaching the node and v is the number of parameters in the linear model for that node (see Witten and Frank, 2005). The features involved in each regression are the features that are tested in the sub-trees below this node (see Wang and Witten, 1997). A smoothing process is then used to avoid steep discontinuities between neighboring linear models at the leaves when predicting continuous class values. During smoothing, the prediction with the leaf model is made first and smoothed by combining it with the predicted values from the linear models at each intermediate node in the path back to the root.

In an aspect of modeling with decision tree algorithms, alternating decision trees (ADTrees) are used herein. This algorithm is a generalization of decision trees that relies on a boosting technique called AdaBoost (see Freund and Schapire (1996), Experiments with a new boosting algorithm. In L. Saitta, editor, Proceedings of the Thirteenth International Conference on machine learning, pages 148-156, San Mateo, Calif., Morgan Kaufmann.) to improve performance.

When compared to other decision tree algorithms, the alternating decision tree algorithm tends to build smaller trees with simpler rules, and therefore be more readily interpretable. It also associates real values with each of the nodes, which allows each node to be evaluated independently from the other nodes. The smaller size of the resulting trees, and the corresponding reduction in memory requirements, makes the alternating decision tree algorithm one of few options for handling very large and complex data sets. The multiple paths followed by a record after a prediction node make this algorithm more robust to missing values because all of the alternative paths are followed in spite of the one ignored path. Finally, this algorithm provides a measure of confidence in each classification, called "classification margin", which in some applications is as important as the classification itself. As with other decision trees, this algorithm is also very robust with respect to multicollinearity among features.

Plants and animals are often propagated on the basis of certain desirable features such as grain yield, percent body fat, oil profile, and resistance to diseases. One of the objectives of a plant or animal improvement program is to identify individuals for propagation such that the desirable features are expressed more frequently or more prominently in successive generations. Learning involves, but is not restricted to, changing the practices, activities, or behaviors involved in identifying individuals for propagation such that the extent of the increase in the expression of the desirable feature is greater or the cost of identifying the individuals to propagate is lower. By accomplishing the steps listed herein, it is possible to develop a model to more effectively select individuals for propagation than by other methods and to more accurately classify or predict the performance of hypothetical individuals based on a combination of feature values.

In addition to the desirable features, data can be obtained for one or more additional features that may or may not have an obvious relationship to the desirable features.

All the citations mentioned in this disclosure are incorporated herein by reference to the extent they relate to the materials and methods used in this disclosure.

EXAMPLE

The following example is for illustrative purposes only and is not intended to limit the scope of this disclosure.

Elite maize lines containing high and low levels of resistance to a pathogen were identified through field and greenhouse screening. A line, which demonstrates high levels of resistance to this pathogen was used as a donor and crossed to a susceptible elite line. The offspring were then backcrossed to the same susceptible elite line. The resulting population was crossed to the haploid inducer stock and chromosome doubling technology was used to develop 191 fixed inbred lines. The level of resistance to the pathogen was evaluated for each line in two replications using field screening methodologies. Forty four replications of the susceptible elite line were also evaluated using field screening methodologies. Genotype data was generated for all 191 double haploid lines, the susceptible elite line and the resistant donor using 93 polymorphic SSR markers.

The final dataset contained 426 samples that were divided in two groups based on the field screening results. Plants with field screening scores ranging from 1 to 4 comprised the susceptible group, while plants with field screening scores ranging from 5 to 9 comprised the resistant group. For our analyses, the susceptible group was labeled with "0" and the resistant group was labeled with "1".

The data set was analyzed using a three step process consisting of: (a) Detecting association rules; (b) Creating new features based on the findings of step (a) and adding these features to the data set; (c) Developing a classification model for a target feature without the features from step (b) and another model with the features from step (b). A description of the application of each of these steps to this data set follows.

Step (a): Detecting Association Rules:

In this example, the 426 samples were evaluated using DDPM (discriminative pattern mining algorithm) and CARPENTER (frequent pattern mining algorithm). All the 94 features (target feature included) were used for evaluation.

The association rule detected by the DDPM algorithm included the following features:
1. Feature 48=5_103.776_umc2013, Feature 59=7_12.353_1gi2132 and Feature 89=10_43.909_phi050
This discriminative pattern has the best information gain (0.068) from all the patterns with support (occurrences out of 426 samples)>=120.

The five association rules detected by the CARPENTER algorithm included the following features:
1. Feature 59=7_12.353_1gi2132, Feature 62=7_47.585_umc1036 and Response=1
2. Feature 59=7_12.353_1gi2132, Feature 92=10_48.493_umc1648 and Response=1
3. Feature 35=4_58.965_umc1964, Feature 59=7_12.353_1gi2132 and Response=1
4. Feature 19=2_41.213_1gi2277, Feature 20=2_72.142_umc1285 and Response=0
5. Feature 19=2_41.213_1gi2277, Feature 78=8_95.351_umc1384 and Response=0
6. Feature 88=10_18.018_umc1576, Feature 89=10_43.909_phi050 and Response=0
The association rules with Response=1 have a support of 180 and rules with Response=0 have a support of 140.

Step (b): Creating New Features Based on the Findings of Step (a) and Adding these Features to the Data Set:

Using the original features included in the 6 association rules detected during step (a), new features were created. These new features were created by concatenating the original features as shown in Table 1.

TABLE 1

Representation of the possible values of a new feature created from two other features.

| Feature 1 | Feature 2 | New Feature |
|---|---|---|
| A | a | aa |
| -B | a | ba |

TABLE 1-continued

Representation of the possible values of a new feature created from two other features.

| Feature 1 | Feature 2 | New Feature |
|---|---|---|
| A | b | ab |
| B | b | bb |

Step (c): Developing a Classification Model for a Target Feature Before Adding the Features from Step (b) and Another Model after Adding the Features from Step (b):

For model development, the REPTree algorithm was applied to the data set. Table 2 shows that after adding the new features to the data set, the mean absolute error decreased (i.e. the new features improved the classification accuracy). Table 3 shows the confusion matrix resulting from a REPTree model using the original data set without the new features from step (b). Table 4 shows the confusion matrix resulting from a REPTree model using the original data set and the new features from step (b). The addition of the new features from step (b) led to an increase in the number of correctly classified records for both classes of the target feature. For class "0", the number of correctly classified records increased from 91 to 97. For class "1", the number of correctly classified records increased from 166 to 175. FIG. 1 shows the increase in the area under the ROC curve obtained with the addition of the new features from step (b). This indicates that adding the new features from step (b) leads to an improved model. These results were obtained using 10-fold cross validation.

TABLE 2

Mean absolute errors obtained from a REPTree model applied to a data set consisting of 426 maize plants using 93 features created from SSR molecular genetic markers with and without the new features from step (b), and the target feature.

| Algorithm | Mean Absolute Error |
|---|---|
| REPTree (Original data) | 0.4438 |
| REPTree (Original data plus new features from step (b)) | 0.436 |

TABLE 3

Confusion matrix resulting from a REPTree model using the original data set without the new features from step (b).

| | Predicted | |
|---|---|---|
| Original | Class-0 | Class-1 |
| Class-0 | 91 | 91 |
| Class-1 | 78 | 166 |

TABLE 4

Confusion matrix resulting from a REPTree model using the original data set and the new features from step (b).

| | Predicted | |
|---|---|---|
| Original | Class-0 | Class-1 |
| Class-0 | 97 | 86 |
| Class-1 | 70 | 175 |

The invention claimed is:

1. A method for selective plant breeding for a continuous target phenotypic feature in plants, the method comprising:
   determining by direct DNA sequencing the genotype of the plants of a plant population for at least one molecular genetic marker selected from the group consisting of a DNA molecular marker and an RNA molecular marker;
   providing an original data set comprising a set of variables, wherein at least one of the variables in the original data set comprises a value representing the genotype of each of the plants for the molecular genetic marker(s);
   determining at least one association rule associating the continuous target phenotypic feature with the variables from the original data set utilizing a computer and one or more association rule mining algorithms;
   utilizing the association rule(s) to create one or more new variables;
   adding the new variable(s) to the original data set to produce a larger data set that contains more variables than the original data set;
   developing a plurality of models for prediction or classification of the continuous target phenotypic feature using all the variables of the larger data set;
   utilizing cross-validation to compare the predictive value of each of the plurality of models, and selecting the model that gives the most accurate prediction of the presence or classification of the continuous target phenotypic feature;
   utilizing the selected model and the larger data set to predict the presence of or classification of the continuous target phenotypic feature in plants comprising specific values for each of the variables in the larger data set;
   utilizing the predicted presence or classification of the continuous target phenotypic feature in plants comprising specific values for each of the variables in the larger data set to select a first parental plant and a second parental plant from the plants of the plant population; and
   breeding the first and second parental plants, thereby forming a progeny plant population comprising the continuous target phenotypic feature.

2. The method according to claim 1, wherein the original data set comprises variables selected from the group consisting of environmental data, phenotypic data, biochemical data, and metabolic data.

3. The method according to claim 1, wherein utilizing the new variable(s) to predict the presence of the continuous target phenotypic feature in the plant comprises utilizing a feature machine learning algorithm.

4. The method according to claim 1, wherein the one or more association rule mining algorithms are selected from the group consisting of direct discriminative pattern mining algorithms and CARPENTER.

5. The method according to claim 1, wherein utilizing the new variable(s) to predict the presence of the continuous target phenotypic feature in the plant comprises utilizing a decision tree selected from the group consisting of the logistic model tree (LMT) algorithm, alternating decision tree (ADTree) algorithm, and M5P algorithm.

6. The method according to claim 1, wherein the original data set comprises a set of variables created from about 93 polymorphic genetic markers.

7. The method according to claim 1, wherein the set of variables includes at least one variable created from a molecular genetic marker selected from the group consisting of a simple sequence repeat (SSR), a cleaved amplified polymorphic sequence (CAPS), a simple sequence length polymorphism (SSLP), a restriction fragment length polymorphism (RFLP), a random amplified polymorphic DNA (RAPD) marker, a single nucleotide polymorphism (SNP), an arbitrary fragment length polymorphism (AFLP), an insertion, a deletion, and a haplotype created from two or more of the above described molecular genetic markers.

8. The method according to claim 1, wherein the set of variables includes at least one variable created from a molecular genetic marker in conjunction with one or more phenotypic measurements, microarray data, analytical measurements, biochemical measurements, or environmental measurements.

9. The method according to claim 8, wherein the set of variables includes at least one variable created from a molecular genetic marker in conjunction with one or more environmental measurements selected from the group consisting of climate and soil characteristics of the field where plants are cultivated.

10. The method according to claim 1, wherein the continuous target phenotypic feature is disease resistance.

11. The method according to claim 1, wherein the continuous target phenotypic feature is a numerically representable phenotypic trait that is adjusted utilizing statistical methods, machine learning methods, or any combination thereof.

12. The method according to claim 1, wherein the continuous target phenotypic feature is hybrid plant performance in plants.

13. The method according to claim 12, wherein the new variable(s) are utilized to predict hybrid performance in plants of the plant population across various geographical locations.

14. The method according to claim 1, wherein the set of variables further includes at least one variable created from a marker selected from the group consisting of a protein molecular marker and a metabolite molecular marker.

15. The method according to claim 1, the method further comprising producing an inbred plant line from the progeny plant.

16. A method for selective plant breeding for a plant comprising pathogen resistance, the method comprising:
   determining by direct DNA sequencing the genotype of a plurality of plants for a plurality of DNA molecular markers, wherein the plurality of plants contains plants having different numerically representable amounts of the pathogen resistance;
   creating an original data set comprising a set of variables representing the genotypes of each of the plants for each of the DNA molecular markers;
   utilizing a discriminative pattern mining algorithm and a CARPENTER algorithm associating the variables of the original data set with the pathogen resistance to create new variables having an association with the pathogen resistance;
   adding the new variables to the original data set to produce a larger data set that contains more variables than the original data set;
   applying a REPTree classification model to the larger data set to predict the amount of pathogen resistance in progeny plants produced from crossing individual plants of the plurality of plants;
   utilizing the predicted amounts of pathogen resistance to select the parent plants of a progeny plant; and crossing the selected parent plants, thereby producing the progeny plant.

17. The method of claim 16, further comprising producing an inbred plant line from the progeny plant.

18. A method for breeding of a plant comprising a numerically representable continuous phenotypic trait by introgressing a DNA segment into an inbred plant line, the method comprising:
   determining by direct DNA sequencing the genotype of a plurality of plants for at least one molecular genetic marker selected from the group consisting of a DNA molecular marker and an RNA molecular marker;
   providing an original data set comprising a set of variables, wherein at least one of the variables in the original data set comprises a value representing the genotype of each of the plants for the molecular genetic marker(s);
   determining at least one association rule associating the numerically representable continuous phenotypic trait with the variables from the original data set utilizing a computer and one or more association rule mining algorithms;
   utilizing the association rule(s) to create one or more new variables;
   adding the new variable(s) to the original data set to produce a larger data set that contains more variables than the original data set;
   developing a plurality of models for prediction or classification of the numerically representable continuous phenotypic trait using all the variables of the larger data set;
   utilizing cross-validation to compare the predictive value of each of the plurality of models, and selecting the model that gives the most accurate prediction of the presence or classification of the numerically representable continuous phenotypic trait;
   utilizing the selected model and the larger data set to predict the presence or classification of the numerically representable continuous phenotypic trait in plants comprising specific values for each of the variables in the larger data set;
   utilizing the predicted presence or classification of the numerically representable continuous phenotypic trait in plants comprising specific values for each of the variables in the larger data set to select a DNA segment for introgression into an inbred plant line; and
   breeding a plant comprising the selected DNA segment with an inbred line to introgress the selected DNA segment into the inbred line.

19. A method for selective plant breeding for a numerically representable continuous phenotypic trait in plants, the method comprising:
   determining by direct DNA sequencing the genotype of the plants of a plant population for at least one molecular genetic marker selected from the group consisting of a DNA molecular marker and an RNA molecular marker;
   providing an original data set comprising a set of variables, wherein at least one of the variables in the original data set comprises a value representing the genotype of each of the plants for the molecular genetic marker(s);
   determining at least one association rule associating the numerically representable continuous phenotypic trait with the variables from the original data set utilizing a computer and one or more association rule mining algorithms;
   utilizing the association rule(s) to create one or more new variables;
   adding the new variable(s) to the original data set to produce a larger data set that contains more variables than the original data set;
   developing a plurality of models for prediction or classification of the numerically representable continuous phenotypic trait using all the variables of the larger data set;
   utilizing cross-validation to compare the predictive value of each of the plurality of models, and selecting the model that gives the most accurate prediction of the presence or classification of the numerically representable continuous phenotypic trait;
   utilizing the selected model and the larger data set to predict the presence or classification of the numerically representable continuous phenotypic trait in hypothetical progeny plants comprising specific values for each of the variables in the larger data set that are able to be obtained by breeding individual pairs of the plants in the plant population;
   utilizing the predicted presence or classification of the numerically representable continuous phenotypic trait in the hypothetical progeny plants to select a pair of the plants in the plant population producing a desired hypothetical progeny plant; and
   breeding the pair of plants, thereby forming a progeny plant population comprising the numerically representable continuous phenotypic trait;
   determining by direct DNA sequencing the genotype of the plants of the progeny plant population for the molecular genetic marker(s);
   providing a progeny plant data set by replacing the variables in the larger data set that comprise a value representing the genotype of a plant for the molecular genetic marker(s) with values representing the genotype of each of the plants in the progeny plant population for the molecular genetic marker(s);
   utilizing the selected model and the progeny plant data set to predict the presence or classification of the numerically representable continuous phenotypic trait in the progeny plants; and
   utilizing the predicted presence or classification of the numerically representable continuous phenotypic trait in the progeny plants to select a progeny plant comprising a desired prediction for the presence or classification of the numerically representable continuous phenotypic trait.

20. The method according to claim 19, the method further comprising producing an inbred plant line from the selected progeny plant.

21. The method according to claim 19, wherein the plant population comprises at least 400 individual plants.

* * * * *